United States Patent

Fryberg et al.

Patent Number: 4,471,048
Date of Patent: Sep. 11, 1984

[54] PHOTOGRAPHIC MATERIAL

[75] Inventors: Mario Fryberg, Praroman-le-Mouret; Viktor Weiss, Fribourg, both of Switzerland

[73] Assignee: Ciba Geigy AG, Basel, Switzerland

[21] Appl. No.: 526,181

[22] Filed: Aug. 24, 1983

Related U.S. Application Data

[62] Division of Ser. No. 391,091, Jun. 22, 1982, Pat. No. 4,436,811.

[30] Foreign Application Priority Data

Jul. 10, 1981 [CH] Switzerland ............ 4545/81

[51] Int. Cl.³ .................................. G03C 5/24
[52] U.S. Cl. ........................................ 430/487
[58] Field of Search ........................... 430/487

[56] References Cited

U.S. PATENT DOCUMENTS

| | | | |
|---|---|---|---|
| 3,346,386 | 10/1967 | Müller et al. | 430/487 |
| 3,385,704 | 5/1968 | Grabhöfer et al. | 430/487 |
| 3,385,708 | 5/1968 | Grabhöfer et al. | 430/487 |
| 4,407,935 | 10/1983 | Fryberg et al. | 430/487 |

Primary Examiner—Mary F. Downey
Attorney, Agent, or Firm—Joseph G. Kolodny

[57] ABSTRACT

Compounds of the formula

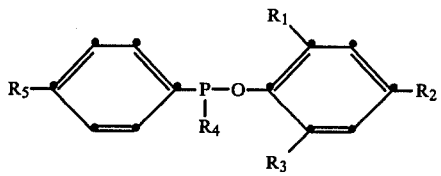

in which $R_1$, $R_2$ and $R_3$ independently of one another are hydrogen, alkyl or alkoxy and $R_2$ additionally represents a radical of the formula

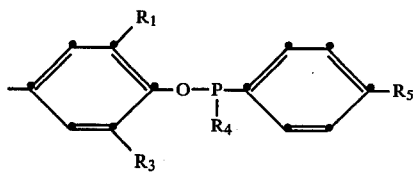

in which $R_1$ and $R_3$ have the abovementioned meanings, $R_4$ is unsubstituted or substituted phenoxy or unsubstituted or substituted amino and $R_5$ is hydrogen or a radical of the formula

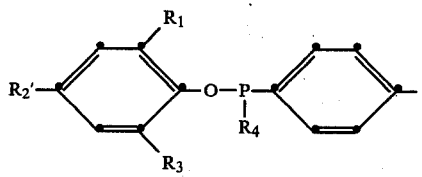

in which $R_1$, $R_3$ and $R_4$ have the abovementioned meanings and $R_2'$ has the same meanings as $R_1$ and $R_3$ are suitable development accelerators in the development of exposed, photographic materials containing silver halide.

They accelerate the reduction of the exposed silver salt to silver and increase the speed of photographic material.

1 Claim, No Drawings

PHOTOGRAPHIC MATERIAL

This is a division of application Ser. No. 391,091, filed June 22, 1982 U.S. Pat. No. 4,436,811.

The present invention relates to photographic recording material which contains at least one development accelerator in at least one silver halide emulsion layer or in a colloid layer adjacent to the silver halide emulsion layer.

It is known that the speed of photographic silver halide emulsions can be increased indirectly or directly by an addition of development accelerators or chemical sensitisers. Compounds of this type have been described, for example in British Patent Specification No. 1,430,998 and in German Offenlegungsschrift No. 2,627,878. In many cases, however, these compounds have only a very weak speed-increasing activity. They also tend to cause fogging and frequently have a very low chemical and thermal stability.

The object of the present invention is thus to provide novel photographic recording materials and developing baths containing development accelerators which have a high speed-increasing activity without at the same time having the disadvantages mentioned.

Phosphorus compounds for use in layers of photographic materials as well as in developing baths have now been found which impart the properties desired to the recording material.

The present invention therefore relates to a photographic recording material which contains at least one development accelerator in at least one silver halide emulsion layer or in a colloid layer adjacent to this layer, wherein the development accelerator is of the formula

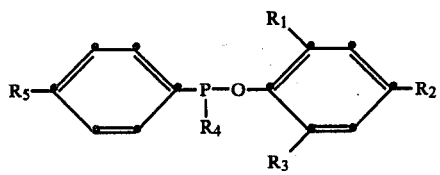
(1)

in which $R_1$, $R_2$ and $R_3$ independently of one another are hydrogen, alkyl having 1 to 16 carbon atoms each or substituted or unsubstituted alkoxy having 1 to 18 carbon atoms each and $R_2$ additionally represents a radical of the formula

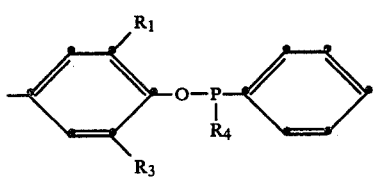

in which $R_1$ and $R_3$ have the abovementioned meaning, $R_4$ is unsubstituted or substituted phenoxy or unsubstituted or substituted amino and $R_5$ is a radical of the formula

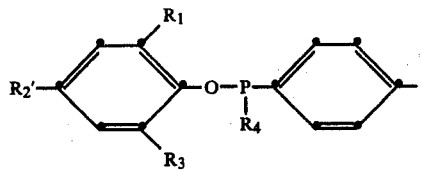

in which $R_1$, $R_3$ and $R_4$ have the abovementioned meanings and $R_2'$ has the same meanings as $R_1$ and $R_3$ or $R_5$ represents hydrogen when $R_2$ is a radical of the formula

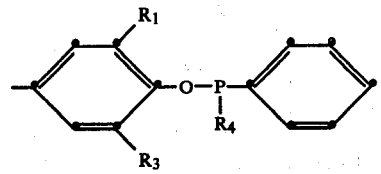

The invention also relates to photographic recording material which contains at least one development accelerator in at least one silver halide emulsion layer or in a colloid layer adjacent to this layer, wherein the development accelerator is a compound having recurring units of the formula

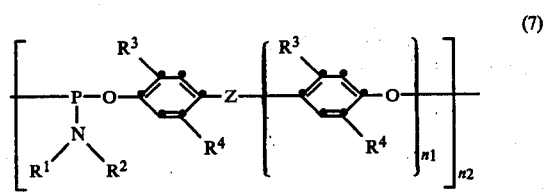
(7)

in which $R^1$ and $R^2$ independently of one another are alkyl having 1 to 12 carbon atoms each or phenyl unsubstituted or substituted by alkyl having 4 to 8 carbon atoms and $R^3$ and $R^4$ independently of one another are hydrogen or alkyl having 1 to 8 carbon atoms each, Z is oxygen or sulfur, $n_1$ is 0, 1 or 2, and $n_2$ is an integer from 1 to 100.

Possible examples of terminal groups for the polymers of the formula (7) are substituted phenol radicals or radicals of the formula

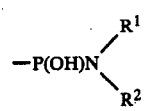

in which $R^1$ and $R^2$ have the abovementioned meanings.

The invention also relates to photographic recording material which contains at least one development accelerator in at least one silver halide emulsion layer or in a colloid layer adjacent to this layer, wherein the development accelerator is of the formula

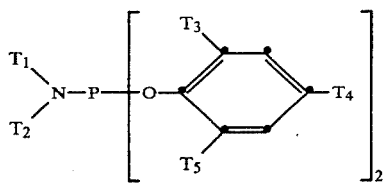 (8)

in which $T_1$ is alkyl having 1 to 12 carbon atoms and $T_2$ is a radical of the formula

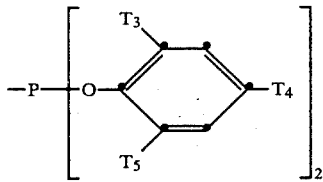

or $T_1$ and $T_2$ are unsubstituted or substituted alkylene having 4 to 12 carbon atoms or form, together with the nitrogen atom to which they are bonded, radicals of the formulae

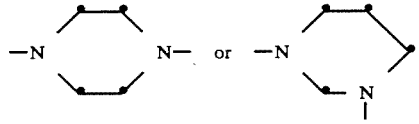

which are substituted, at the further nitrogen atom, by a radical of the formula

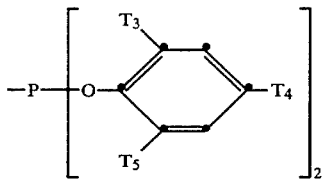

and $T_3$, $T_4$ and $T_5$ independently of one another are hydrogen or alkyl having 1 to 12 carbon atoms each.

The invention further relates to the development accelerators of the formulae (1) to (10) contained in the photographic recording materials.

The invention moreover relates to the use of the photographic recording materials for the production of photographic images.

Furthermore, the invention relates to a developing bath for the photographic recording materials and containing the development accelerators of the formulae (1) to (10).

Moreover, the invention relates to a process for the preparation of photographic recording materials containing development accelerators of the formulae (1) to (10).

The invention also relates to compounds of the formulae (11) and (12).

The substituents $R_1$, $R_2$ and $R_3$ in the compounds of formula (1) represent, in addition to hydrogen, alkyl having 1 to 16 carbon atoms each. The alkyl chains can be unbranched or, preferably, branched. Examples of suitable alkyl radicals are methyl, ethyl, propyl, i-propyl, butyl, i-butyl, tert.-butyl, amyl, tert.-amyl (1,1-dimethylpropyl), 1,1,3,3-tetramethylbutyl, 1-methylethylpentyl, hexyl, 1-methylpentyl, neopentyl, 1-, 2- and 3-methylhexyl, heptyl, n-octyl, tert.-octyl, 2-ethylhexyl, n-nonyl, isononyl, tert.-nonyl, decyl, tert.-decyl, undecyl and also dodecyl, tetradecyl and hexadecyl as well as their corresponding isomers.

Of these radicals those are preferred which have 1 to 12, in particular 1 to 8, carbon atoms. Alkyl radicals having 4 to 8 carbon atoms, and in particular their branched isomers, are particularly suitable.

Alkoxy radicals $R_1$, $R_2$ and $R_3$ are, for example, alkoxy radicals having 1 to 18 carbon atoms each. Suitable radicals are derived from the alkyl radicals indicated above for $R_1$, $R_2$ and $R_3$. Octadecyl and corresponding isomers are additionally possible. Alkoxy radicals having 1 to 14 carbon atoms are particularly preferred. The alkoxy radicals can be substituted, for example by further alkoxy radicals having 1 to 4 carbon atoms, phenoxy or carbalkoxy having 2 to 5, in particular 2 or 3, carbon atoms.

The substituent $R_2$ additionally represents a radical of the formula

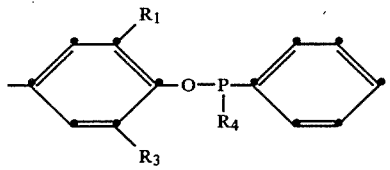

in which $R_1$ and $R_3$ have the abovementioned meanings.

The substituents $R_1$, $R_2$ and $R_3$ can have the meanings assigned to them above independently of one another.

$R_4$ represents unsubstituted or substituted phenoxy. The phenoxy radical can be substituted in the ortho-positions and the para-position and be of the formula

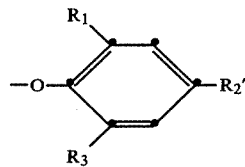

in which $R_1$ and $R_3$ have the abovementioned meanings. The radical $R_2'$ has the same meanings as $R_1$ and $R_3$.

$R_4$ is also the radical of a substituted amine which can be illustrated, for example by a radical

in which $R_6$ and $R_7$ represent alkyl having 1 to 24 carbon atoms each. Examples of suitable alkyl radicals have been indicated above for $R_1$, $R_2$ and $R_3$. Octadecyl, nonadecyl, eicosyl, docosyl, tetracosyl and their isomers are also possible. $R_6$ and $R_7$ also represent cycloalkyl having 5 to 8 carbon atoms. Cyclopentyl and cyclohexyl are particularly preferred. $R_6$ and $R_7$ also represent phenyl. The phenyl radical is unsubstituted or substituted, preferably in the ortho-position(s) and/or the para-position, by alkyl having 4 to 8 carbon atoms. $R_6$ and $R_7$ further represent a radical of the formula

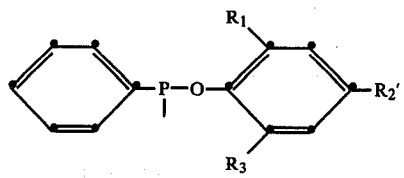

in which $R_1$, $R_2'$ and $R_3$ have the abovementioned meanings. $R_6$ and $R_7$ also form, together with the nitrogen atom to which they are bonded, unsubstituted or substituted heterocyclic radicals which preferably contain nitrogen atoms and are in particular of the formulae

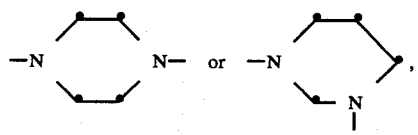

the free valencies of the nitrogen atoms being saturated by a radical of the formula

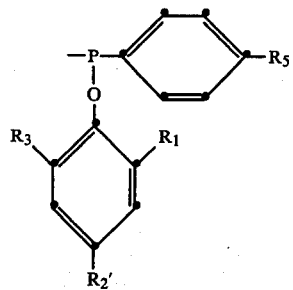

in which $R_1$, $R_2'$ and $R_3$ have the abovementioned meanings.

The substituents $R_6$ and $R_7$ can have the abovementioned meanings independently of each other.

The substituent $R_5$ represents a radical of the formula

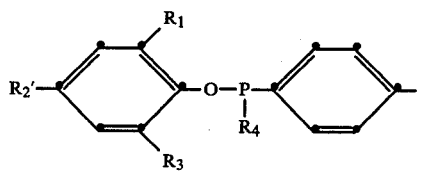

in which $R_1$, $R_2'$, $R_3$ and $R_4$ have the abovementioned meanings. When $R_2$ is a radical of the formula

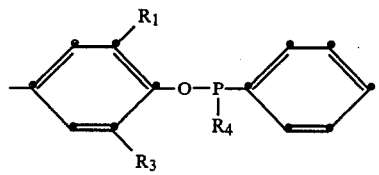

$R_5$ represents hydrogen.

Those alkyl groups suitable for use as radicals $R^1$, $R^2$, $R^3$ and $R^4$ in compounds of the formula (7) have already been listed in the explanations for $R_1$ in the formula (1). Preferably, $R^1$ and $R^2$ independently of one another are alkyl having 4 to 10 carbon atoms each, $R^3$ and $R^4$ are hydrogen or alkyl having 4 to 8 carbon atoms, Z is preferably oxygen, $n_1$ is 0 and $n_2$ is an integer from 10 to 20.

Alkyl radicals suitable for use as radicals $T_1$, $T_3$, $T_4$ and $T_5$ in compounds of the formula (8) are those already listed in the explanations, for example, of $R_1$. $T_1$ preferably is alkyl having 1 to 6 carbon atoms and $T_3$, $T_4$ and $T_5$ preferably are hydrogen or, in each case, alkyl having 4 to 8 carbon atoms. The alkylene radicals formed by $T_1$ and $T_2$ can be substituted, for example by alkyl groups for example methyl, ethyl or tert.-butyl.

Preferred development accelerators are of the formula

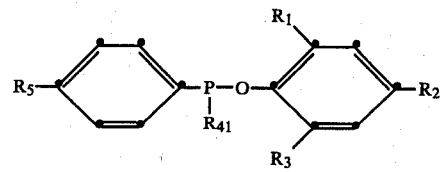

(2)

in which $R_{41}$ is a radical of the formula

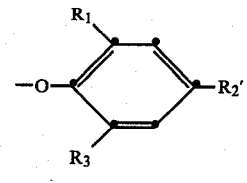

in which $R_1$, $R_2'$ and $R_3$ have the abovementioned meanings or a radical of the formula

in which $R_6$ and $R_7$ independently of one another are alkyl having 1 to 24 carbon atoms each, cyclopentyl, cyclohexyl, unsubstituted or substituted phenyl or a radical of the formula

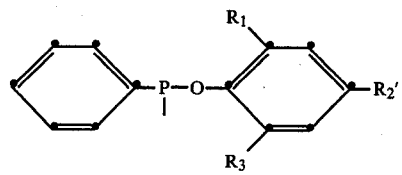

in which $R_1$, $R_2'$ and $R_3$ have the abovementioned meanings or $R_6$ and $R_7$, together with the nitrogen atom to which they are bonded, form radicals of the formulae

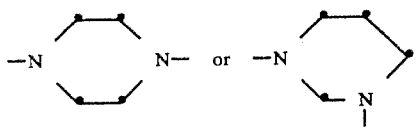

which are substituted, at the further nitrogen atom, by a radical of the formula

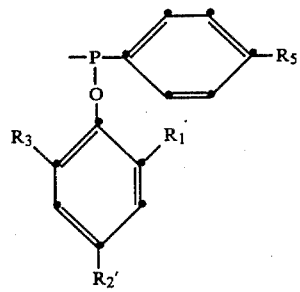

in which $R_1$, $R_2'$, $R_3$ and $R_5$ have the abovementioned meanings.

Particularly suitable development accelerators are those of the formula

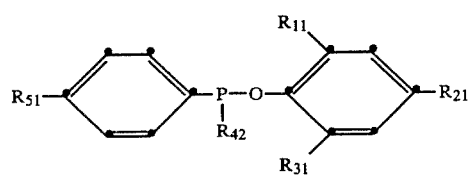
(3)

in which $R_{42}$ is a radical of the formula

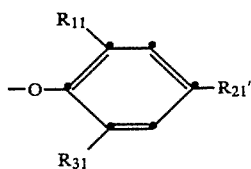

in which $R_{11}$, $R_{21}'$ and $R_{31}$ independently of one another represent hydrogen, alkyl having 1 to 12 carbon atoms each, or alkoxy which has 1 to 14 carbon atoms and which is unsubstituted or substituted by carbalkoxy having 2 to 5 carbon atoms or $R_{42}$ is a radical of the formula

in which $R_{61}$ and $R_{71}$ independently of each other are alkyl having 1 to 18 carbon atoms each, cyclopentyl, cyclohexyl, phenyl substituted by alkyl having 1 to 8 carbon atoms or a radical of the formula

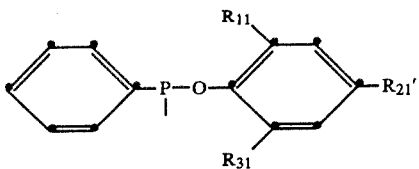

in which $R_{11}$, $R_{21}'$ and $R_{31}$ have the abovementioned meanings or $R_{61}$ and $R_{71}$, together with the nitrogen atom to which they are bonded, form radicals of the formulae

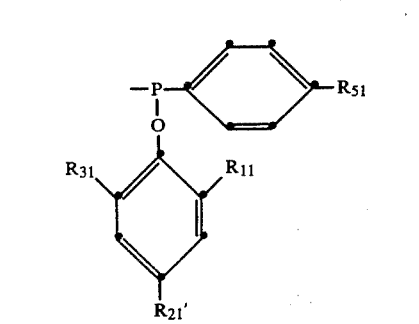

which are substituted, at the further nitrogen atom, by a radical of the formula

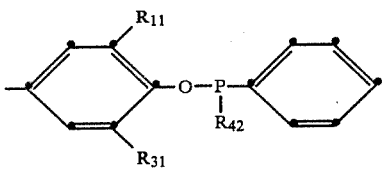

in which $R_{11}$, $R_{21}'$ and $R_{31}$ have the abovementioned meanings, $R_{21}$ has the same meaning as $R_{11}$ and $R_{31}$ and additionally represents a radical of the formula

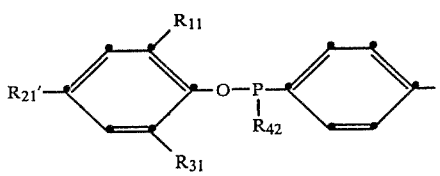

in which $R_{11}$, $R_{31}$ and $R_{42}$ have the abovementioned meanings and $R_{51}$ is a radical of the formula in which $R_{11}$, $R_{21}'$, $R_{31}$ and $R_{42}$ have the abovementioned meanings or $R_{51}$ represents hydrogen when $R_{21}$ is a radical of the formula

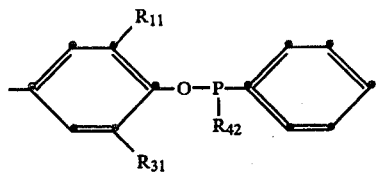

Other preferred development accelerators are of the formula

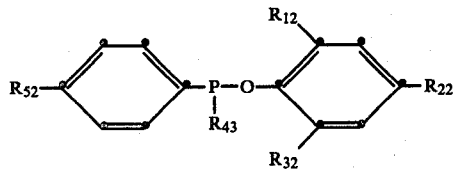  (4)

in which $R_{43}$ is a radical of the formula

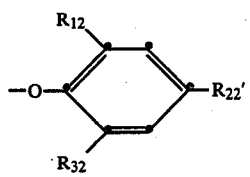

in which $R_{12}$, $R_{22}'$ and $R_{32}$ independently of one another are hydrogen, alkyl having 1 to 8 carbon atoms each or alkoxy which has 1 to 14 carbon atoms and which is unsubstituted or substituted by carbalkoxy having 2 or 3 carbon atoms or $R_{43}$ is a radical of the formula

in which $R_{62}$ and $R_{72}$ independently of each other are alkyl having 1 to 12 carbon atoms each or a radical of the formula

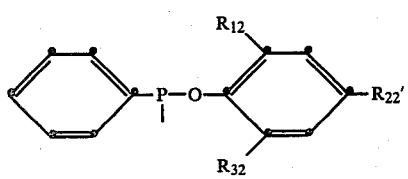

in which $R_{12}$, $R_{22}'$ and $R_{32}$ have the abovementioned meanings or $R_{62}$ and $R_{72}$, together with the nitrogen atom to which they are bonded, form a radical of the formula

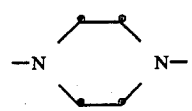

which is substituted, at the further nitrogen atom, by a radical of the formula

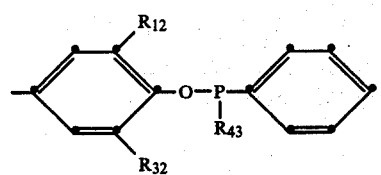

in which $R_{12}$, $R_{22}'$ and $R_{32}$ have the abovementioned meanings, $R_{22}$ has the same meaning as $R_{12}$ and $R_{32}$ and additionally represents a radical of the formula

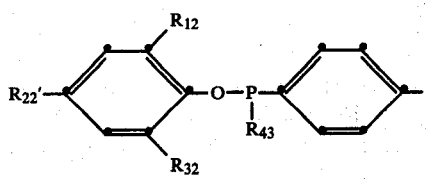

in which $R_{12}$, $R_{32}$ and $R_{43}$ have the abovementioned meanings and $R_{52}$ is a radical of the formula

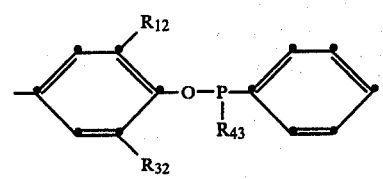

in which $R_{12}$, $R_{22}'$, $R_{32}$ and $R_{43}$ have the abovementioned meaning or $R_{52}$ is hydrogen where $R_{22}$ is a radical of the formula

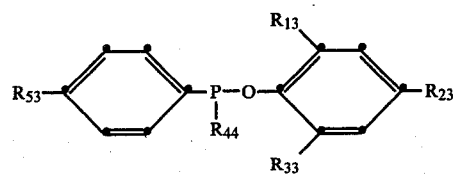

Of interest are also development accelerators of the formula

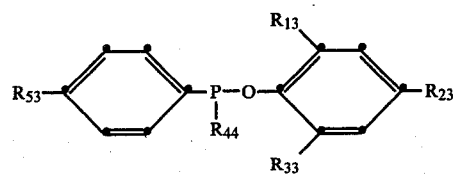  (5)

in which $R_{44}$ is a radical of the formula

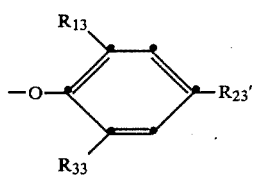

in which $R_{13}$, $R_{23}'$ and $R_{33}$ independently of one another are hydrogen, alkyl having 4 to 8 carbon atoms each or alkoxy which has 1 to 14 carbon atoms and is unsubstituted or substituted by carbalkoxy having 2 or 3 atoms or $R_{44}$ is a radical of the formula

in which $R_{63}$ and $R_{73}$ independently of each other are alkyl having 1 to 8 carbon atoms each or a radical of the formula

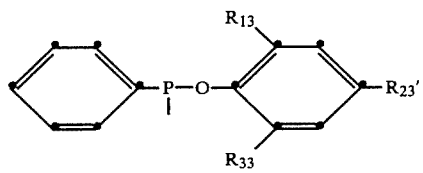

in which $R_{13}$, $R_{23}'$ and $R_{33}$ have the abovementioned meanings or $R_{63}$ and $R_{73}$, together with the nitrogen atom to which they are bonded, form a radical of the formula

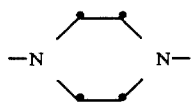

which is substituted, at the further nitrogen atom, by a radical of the formula

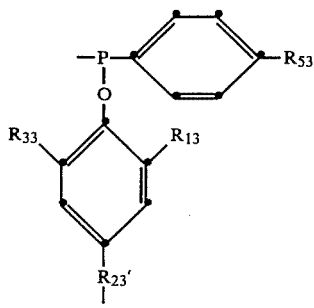

in which $R_{13}$, $R_{23}'$ and $R_{33}$ have the abovementioned meanings, $R_{23}$ has the same meaning as $R_{13}$ and $R_{33}$ and additionally represents a radical of the formula

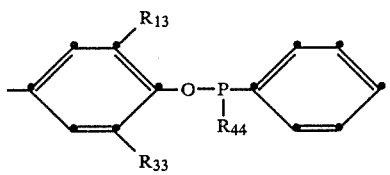

in which $R_{13}$, $R_{33}$ and $R_{44}$ have the abovementioned meanings and $R_{53}$ is a radical of the formula

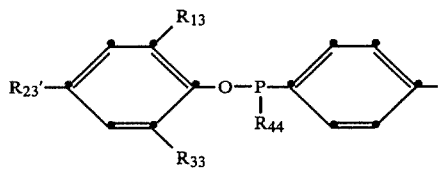

in which $R_{13}$, $R_{23}'$, $R_{33}$ and $R_{44}$ have the abovementioned meanings or $R_{53}$ is hydrogen when $R_{23}$ is a radical of the formula

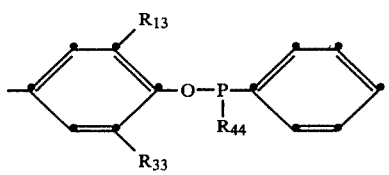

Valuable development accelerators are of the formula

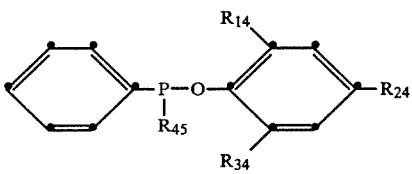 (6)

in which $R_{45}$ is a radical of the formula

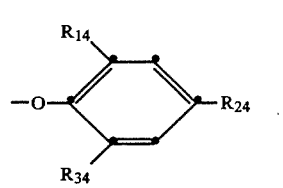

in which $R_{14}$ and $R_{34}$ independently of each other are hydrogen or alkyl having 4 to 8 carbon atoms each and $R_{24}$ is hydrogen, alkyl having 4 to 8 carbon atoms each or alkoxy which has 1 to 14 carbon atoms and is unsubstituted or substituted by carbalkoxy having 2 or 3 carbon atoms or $R_{45}$ is a radical of the formula

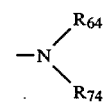

in which $R_{64}$ and $R_{74}$ independently of each other are alkyl having 1 to 8 carbon atoms each or a radical of the formula

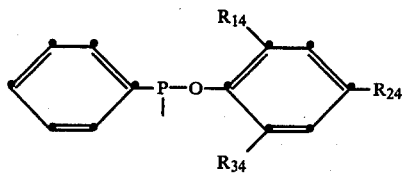

in which $R_{14}$, $R_{24}$ and $R_{34}$ have the abovementioned meanings or $R_{63}$ and $R_{73}$, together with the nitrogen atom to which they are bonded, form a radical of the formula

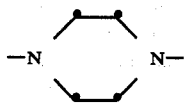

which is substituted by a radical of the formula

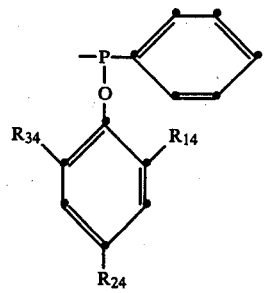

in which $R_{14}$, $R_{24}$ and $R_{34}$ have the abovementioned meanings.

Further suitable development accelerators contain recurring units of the formula

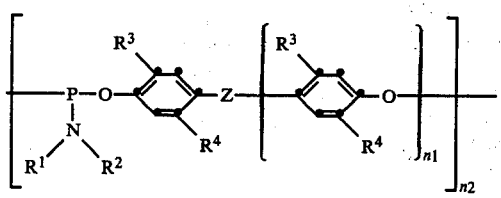
(7)

in which $R^1$ and $R_2$ independently of each other are alkyl having 1 to 12 carbon atoms each or phenyl which is unsubstituted or substituted by alkyl having 4 to 8 carbon atoms and $R^3$ and $R_4$ independently of each other are hydrogen or alkyl having 1 to 8 carbon atoms each, Z is oxygen or sulfur, $n_1$ is 0, 1 or 2 and $n_2$ is an integer from 1 to 100.

Other suitable development accelerators are of the formula

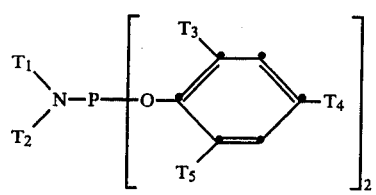
(8)

in which $T_1$ is alkyl having 1 to 12 carbon atoms and $T_2$ is a radical of the formula

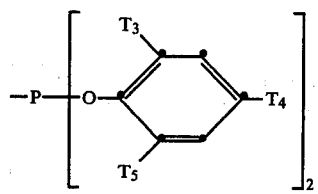

or $T_1$ and $T_2$ are unsubstituted or substituted alkylene having 4 to 12 carbon atoms or form, together with the nitrogen atom to which they are bonded, radicals of the formulae

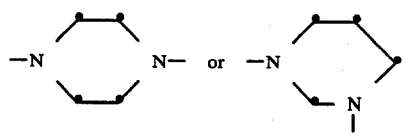

which are substituted, at the further nitrogen atom, by a radical of the formula

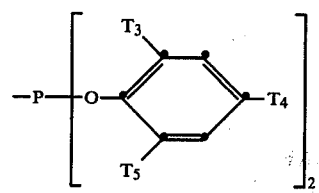

and $T_3$, $T_4$ and $T_5$ independently of one another are hydrogen or alkyl having 1 to 12 carbon atoms each.

Suitable development accelerators of the formula (8) are those of the formula

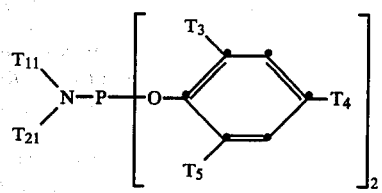
(9)

in which $T_{11}$ is alkyl having 1 to 6 carbon atoms, $T_{21}$ is a radical of the formula

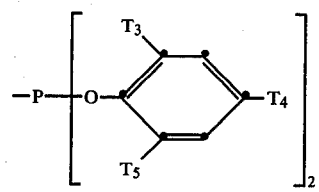

or $T_{11}$ and $T_{21}$ are a group of the formula —C(CH$_3$)$_2$CH$_2$CH$_2$CH$_2$C(CH$_3$)$_2$— or form, together with the nitrogen atom to which they are bonded, a radical of the formula

which is substituted, at the further nitrogen atom, by a radical of the formula

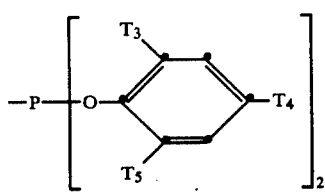

and $T_3$, $T_4$ and $T_5$ have the abovementioned meanings.

Suitable development accelerators of the formula (9) are those of the formula

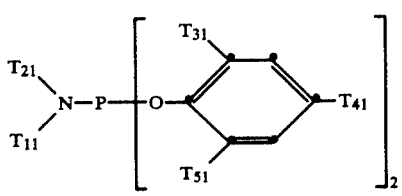 (10)

in which $T_{31}$, $T_{41}$ and $T_{51}$ each are hydrogen or alkyl having 4 to 8 carbon atoms each and $T_{11}$ and $T_{21}$ have the abovementioned meanings.

The development accelerators employed according to the invention are used in contact with the silver halide emulsion layer. This means that they must be present in the emulsion layer during development. This can be ensured either by incorporating the compounds into the emulsion layer before exposure, or by making it possible for the compounds to diffuse from a developing bath into the emulsion layer. This is possible since the development accelerators are stable to hydrolysis and can therefore be present in the dissolved state in a processing bath for a prolonged period. It is preferred to incorporate the compounds directly into the silver halide emulsion. It is possible to use either aqueous solutions of these compounds or solutions in an organic solvent which does not affect the photogaphic properties of the light-sensitive material. If it is intended to use the development accelerators in a developing bath, a conncentration of 0.5 to 10 g per liter of solution is preferably chosen.

The speed-increasing compounds used according to the invention can be added to the emulsion at various times during the preparation of the emulsion. For example, they can be added, individually or in a mixture with other conventional additives, during the physical or chemical ripening or at any other time before coating of the emulsion. Most preferably, however, this is carried out after chemical ripening and shortly before coating of the emulsion.

The quantity added depends on the compound selected and on the type of colloidal binder used for the silver halide emulsion. In general, the compounds according to the present invention are used in a quantity of 1 to 50 g per mol of silver halide.

Customary methods can be used for incorporating the compounds into the silver halide emulsions. For example, solutions in high-boiling solvents hardly miscible with water, for example di-n-butyl naphthalate or tricresyl phosphate, or in low-boiling solvents hardly miscible with water, such as ethyl acetate, methylene chloride, chloroform or the like, or mixtures thereof, can be used for incorporation. For this purpose, these solutions are dispersed in extremely fine droplets, preferably in the presence of a wetting agent or dispersant, in the hydrophilic colloidal medium. The low-boiling solvent which hardly mixes with water is then evaporated off. Of course, any other technique known to those skilled in the art, for incorporating additives into colloid mixtures, can be used. For example, water-soluble substances which contain a sulfo group (in the acid form or salt form) conferring solubility in water can be incorporated, from an aqueous or alkaline solution, in the coating composition for the particular layer.

The hydrophilic colloid composition in which the compounds according to the invention are dispersed or dissolved does not absolutely have to be the coating composition for the silver halide emulsion layer itself, which should contain them. Advantageously, the compounds can initially be dispersed or dissolved in an aqueous, light-insensitive, hydrophilic colloid solution, whereupon the resulting mixture, optionally after removal of the organic solvents, is intimately mixed shortly before application with the coating composition for the light-sensitive silver halide emulsion layer.

Thus, for example, polymeric or copolymeric latices can be charged with the compounds according to the invention, optionally in the presence of an organic solvent. The mixture thus obtained is then admixed, before application, to the light-sensitive silver halide emulsion.

Owing to their property of assisting the developability of photographic layers, the compounds used according to the invention are outstandingly suitable for increasing the X-ray light-sensitivity, for example, and the general light-sensitivity of orthochromatic, panchromatic and other special emulsions as well as of conventional emulsions not spectrally sensitised. The substances can be added to these emulsions either separately from or together with conventional sensitising dyes. It may also be mentioned that the described advantages of the compounds used according to the invention are applicable not only to negative emulsions but also to positive emulsions.

The novel compounds are advantageous for developing light-sensitive materials intended for the reproduction of graphical illustrations.

In the silver dye bleach process, in which, after a first black-and-white development, the incorporated dye, with the aid of the silver image formed, is bleached imagewise proportionally to the quantity of silver, the compounds according to the invention are very particularly suitable. In their presence, considerably larger quantities of silver are developed after exposure of the material, and this subsequently manifests itself in better and more complete bleaching of the dye. Due to better utilisation of the silver coated in, it is also possible to save quite considerable quantities of silver.

The developer substances known to those skilled in the art can be used as the developer. The method of processing corresponds to the methods customarily used for the particular photographic material.

PREPARATION EXAMPLES

Example 1

262 g (1.0 mol) of 2,4,6-tri-tert.-butylphenol are heated to 70°–75° C. in 600 ml of triethylamine. 179 g (1.0 mol) of P,P-dichlorophenylphosphine are added dropwise in the course of 2 hours under an atmosphere of nitrogen and with moisture excluded. The reaction mixture is then maintained at 80°–90° C. for 20 hours. After digestion of the reaction mixture in 2,000 ml of petroleum ether, triethylammonium chloride is filtered off with suction. The filtrate is evaporated to dryness, and the residue (red-brown oil) is recrystallised from acetonitrile. 311 g of colourless crystals of an intermediate having a melting point of 93°–96° C. (decomposition) are obtained.

60.6 g (0.15 mol) of this intermediate are heated for 24 hours at 90° C. with the exclusion of moisture together with 19.4 g (0.15 mol) of di-n-butylamine in 250 ml of toluene in the presence of 30 ml of triethylamine and 1 ml of dimethylformamide. The reaction mixture is extracted with water and then evaporated to dryness. The residue obtained amounts of 68 g of an orange-coloured oil which is recrystallised from ethanol. 46 g of colourless crystals (62%), melting point 80°–82° C. (decomposition) of the compound of the formula

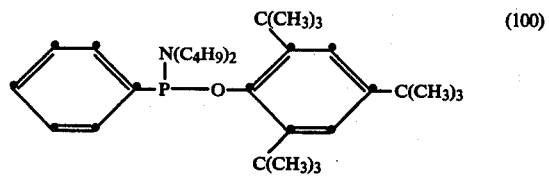
(100)

are obtained.

The following compounds can also be prepared according to Example 1:

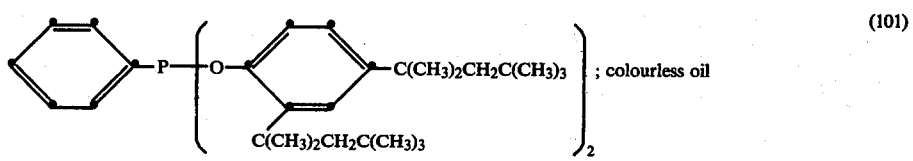
(101) ; colourless oil

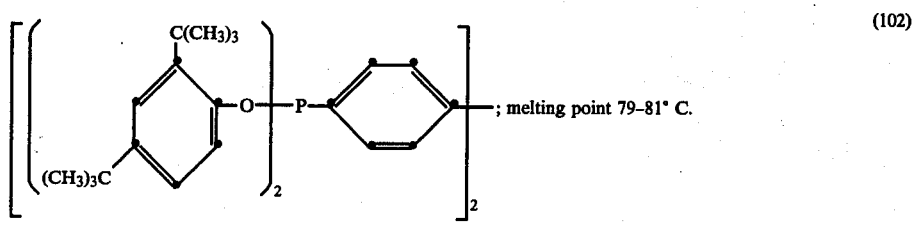
(102) ; melting point 79–81° C.

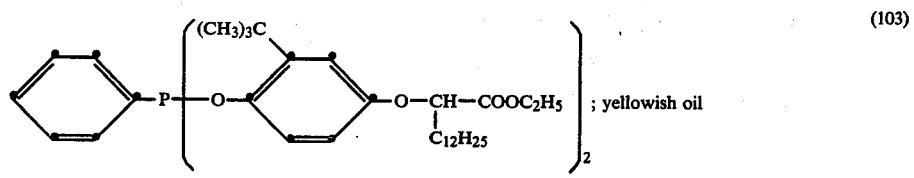
(103) ; yellowish oil

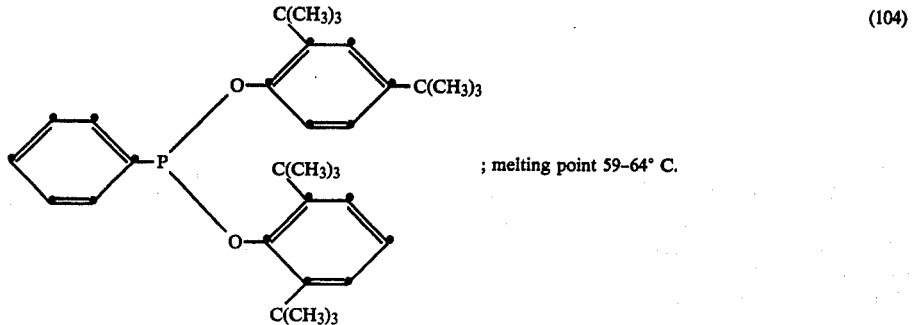
(104) ; melting point 59–64° C.

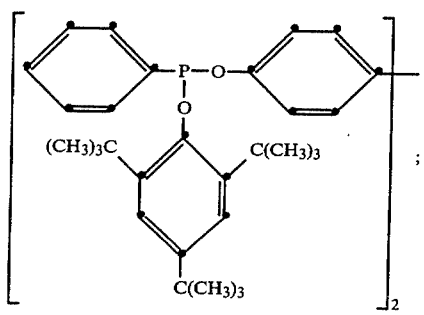 (105); melting point 114.5–117° C.

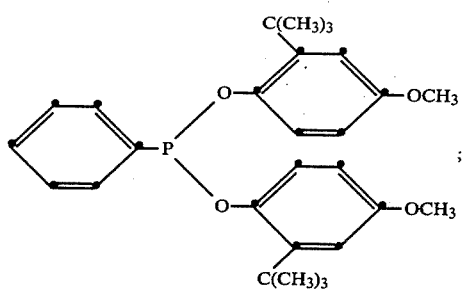 (106); melting point 81–82.5° C.

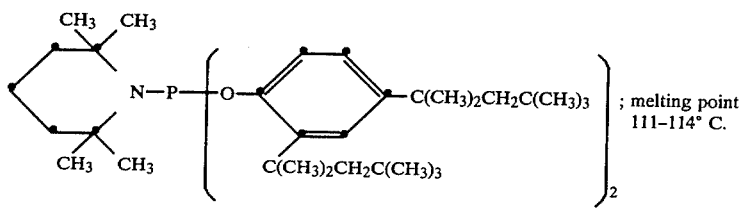 (107); melting point 111–114° C.

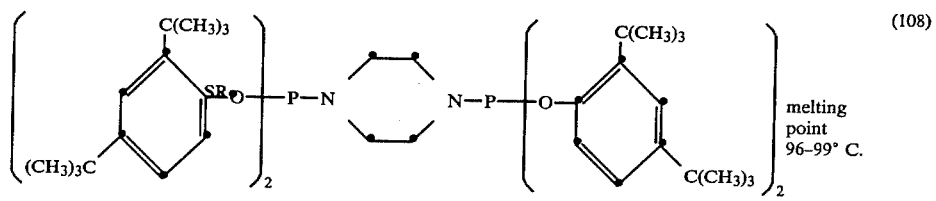 (108) melting point 96–99° C.

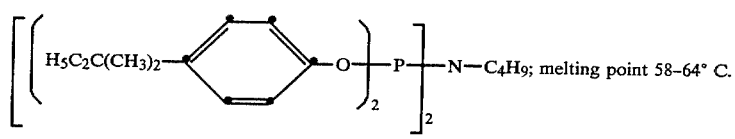 (109); melting point 58–64° C.

Example 2

11.5 g of di-tert.-butyl hydroquinone and 14.3 ml of triethylamine are initially introduced into 200 ml of toluene. A solution of 12.1 g of N',N'-di-[2-ethylhexane]-aminodichlorophosphine in 60 ml of toluene is added at room temperature. The mixture is refluxed for 20 hours and thereafter cooled down to room temperature, the resulting salt is filtered off, and the filtrate is concentrated. The resulting resin is washed with hot acetonitrile, filtered off with suction, pulverised and dried. It is possible, on the basis of the NMR spectrum, to assign the following structural formula

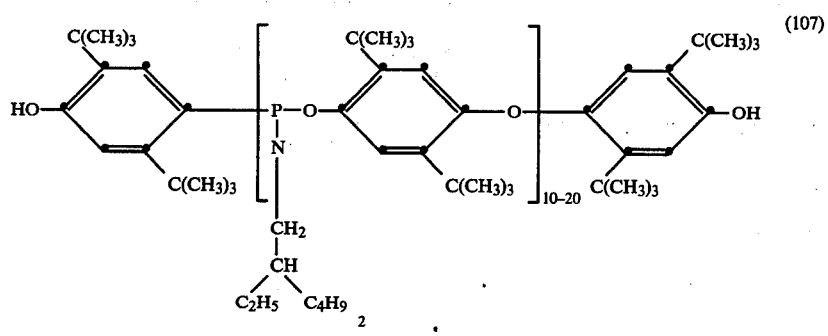

to the product obtained.

The product sinters at 150°–200° C.

APPLICATION EXAMPLES

Example 3

The quantities of development accelerator indicated in Table 1 are in each case dissolved in a mixture of 534 mg of tricresyl phosphate and 20 ml of ethyl acetate. 140 ml of an aqueous 6% gelatin solution and 1 ml of an 0.8% solution of diisobutylnaphthalenesulfonic acid (sodium salt) are added to the first solution. The mixture is emulsified for 5 minutes by means of an ultrasonic apparatus. A silver halide emulsion having a total silver content of 0.6 g of silver and an aqueous solution of the hardener of the formula

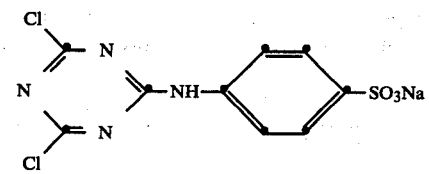

are added.

The mixture is coated at about 40° C. onto polyethylene-coated paper and dried at room temperature.

The sample is exposed under a 5-step wedge ($\Delta=0.15$) with 200 lux and processed as follows:

3 minutes developing
1 minute washing
3 minutes fixing
4 minutes washing, followed by drying.

The processing baths used have the customary compositions known in photography.

Black-and-white images of the wedge and having the parameters described in Table 1 are obtained.

TABLE 1

| Sample | Development accelerator | (Compound No.) | Quantity of development accelerator coated in [mg] | Measured grey densities × 100 at steps 1 | 2 | 3 | 4 |
|---|---|---|---|---|---|---|---|
| 1. | Control | | 0 | 39 | 62 | 78 | 81 |
| 2. | [structure] | (104) | 173 | 62 | 82 | 93 | 93 |
| 3. | [structure] | (103) | 324 | 67 | 86 | 94 | 99 |

TABLE 1-continued

| Sample | Development accelerator | (Compound No.) | Quantity of development accelerator coated in [mg] | Measured grey densities × 100 at steps | | | |
|---|---|---|---|---|---|---|---|
| | | | | 1 | 2 | 3 | 4 |
| 4. | [phenyl-P(-O-aryl)$_2$ structure with C(CH$_3$)$_3$ substituents]$_2$ | (105) | 158 | 79 | 94 | 100 | 107 |

This table clearly shows that, over the entire exposure range, the silver densities obtained on identical exposure and development in the presence of the compounds according to the invention are higher.

Example 4

Coatings corresponding to Example 3 are prepared, except that the development accelerators indicated in Table 2 are used. The samples are exposed for two seconds under a 5-step wedge with 200 lux and processed as in Example 3. The developed, metallic silver on the individual steps is determined by X-ray fluorimetry. The results obtained are shown in Table 2.

TABLE 2

| Sample | Development accelerator | (Compound No.) | Quantity of development accelerator coated in [mg] | Measured quantity of silver in mg on step | | | |
|---|---|---|---|---|---|---|---|
| | | | | 1 | 2 | 3 | 4 |
| 1. | Blank | | 0 | 129 | 276 | 371 | 365 |
| 2. | phenyl-P(-O-aryl with C(CH$_3$)$_3$ groups)(N(C$_4$H$_9$)$_2$) | (100) | 170 | 253 | 368 | 400 | 435 |
| 3. | phenyl-P(-O-aryl with C(CH$_3$)$_3$ and OCH$_3$)$_2$ | (106) | 157 | 271 | 366 | 417 | 423 |
| 4. | (CH$_3$)$_3$C, HO-aryl-[P(-O-aryl-O-)$_{10-20}$-aryl-OH](N[CH$_2$-CH(C$_2$H$_5$)(C$_4$H$_9$)]$_2$) with C(CH$_3$)$_3$ substituents | (107) | 158 | 289 | 411 | 499 | 529 |

Larger quantities of developed silver are measured on all steps with the addition of development accelerators under identical conditions.

Example 5

Coatings according to Example 3 are prepared, except that they contain the dyestuff of the formula

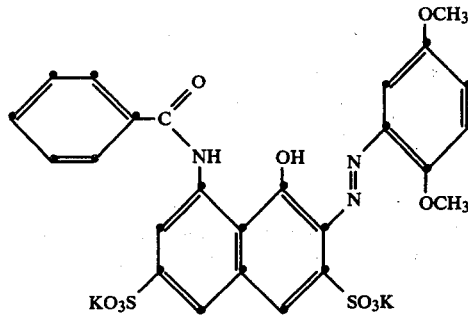
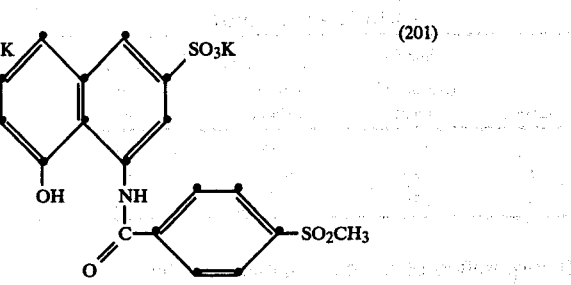

(201)

as a further component. In addition, a sample is prepared without development accelerator for use as a control.

The samples are exposed for 2 seconds under a 21-step wedge with 500 lux and then processed at 30° C. as follows:

| 1. Development | 3 minutes |
|---|---|
| 2. Washing | 1 minute |
| 3. Dye bleach | 3 minutes |
| 4. Washing | 1 minute |
| 5. Fixing | 3 minutes |
| 6. Washing | 4 minutes |

The processing baths 1 and 5 have customary compositions. The dye bleach bath 3, however, is composed as follows:

| 1,950 ml of water |
|---|
| 56 ml of concentrated sulfuric acid |
| 2 ml of mercaptosuccinic acid |
| 18 g of sodium iodide |
| 12 g of the disodium salt of 4-nitrophenol-2-sulfonic acid |
| 2 g of 6-methoxy-2,3-dimethylquinoxaline | a greater extent over the entire exposure range, due to greater quantities of developed silver.

Example 6

Coatings are prepared according to Example 5. 258 mg of the development accelerator of the formula (102) are used per gram of silver coated in. A sample without development accelerator is prepared for use as a control.

The samples are exposed for 2 seconds under a continuous wedge with 500 lux and processed according to Example 5, except that the dye bleach is carried out for different times.

Cyan wedges having an absorption maximum at 618 nm and a maximum density of 2.2 are obtained. The amount of light log E (0.6) necessary to develop the amount of silver required for obtaining an optical density of 0.6 was determined from curves showing optical density as a function of the amount of light.

Since the extent of dye bleach is proportional to the amount of silver developed, the speed of the particular photographic material concerned can be inferred in this way. The following results are obtained:

TABLE 3

| Sample | Development accelerator (Compound No.) | Quantity of development accelerator employed [mg] | Measured density × 100 on step | | | | | | |
|---|---|---|---|---|---|---|---|---|---|
| | | | 1 | 3 | 6 | 9 | 12 | 15 | 20 |
| 1. | Blank | 0 | 24 | 57 | 126 | 202 | 245 | 254 | 243 |
| 2. | (100) | 170 | 3 | 15 | 74 | 128 | 193 | 235 | 246 |
| 3. | (102) | 177 | 5 | 18 | 84 | 135 | 200 | 240 | 242 |

Clear, sharp cyan wedges having an absorption maximum at 618 nm and the densities indicated in Table 3 are obtained.

This comparison shows that, with an addition of development accelerator, the coated-in dye is bleached to

TABLE 4

| Sample | Time for dye bleach (sec) | log E (0.6) without accelerator | log E (0.6) with accelerator |
|---|---|---|---|
| 1 | 32 | 0.81 | 0.68 |
| 2 | 45 | 0.80 | 0.65 |
| 3 | 64 | 0.75 | 0.65 |
| 4 | 90 | 0.74 | 0.64 |

TABLE 4-continued

| Sample | Time for dye bleach (sec) | log E (0.6) without accelerator | log E (0.6) with accelerator |
|---|---|---|---|
| 5 | 127 | 0.75 | 0.63 |
| 6 | 180 | 0.73 | 0.64 |
| 7 | 254 | 0.70 | 0.64 |

Incorporation of the development accelerator in the photographic material thus increases the speed of the material independently of the dye bleach time, with otherwise identical exposure and development.

What is claimed is:

1. A developing bath for photographic recording material, which contains a developing agent and 0.5 to 10 g of a development accelerator, per liter of solution, of the formula

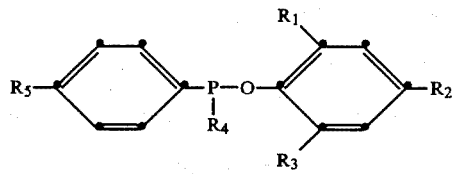 (1)

in which $R_1$, $R_2$ and $R_3$ independently of one another are hydrogen, alkyl having 1 to 16 carbon atoms each or substituted or unsubstituted alkoxy having 1 to 18 carbon atoms each and $R_2$ additionally represents a radical of the formula

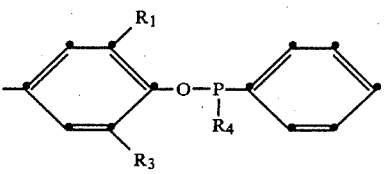

in which $R_1$ and $R_3$ have the above mentioned meaning, $R_4$ is unsubstituted or substituted phenoxy or unsubstituted or substituted amino and $R_5$ is a radical of the formula

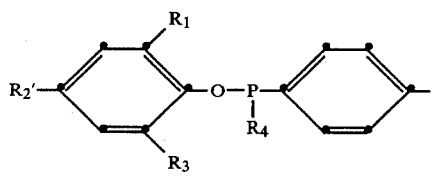

in which $R_1$, $R_3$ and $R_4$ have the above mentioned meanings and $R_2'$ has the same meanings as $R_1$ and $R_3$ or $R_5$ represents hydrogen when $R_2$ is a radical of the formula

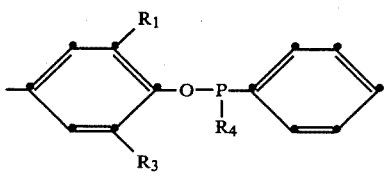

* * * * *